United States Patent [19]

Pfister

[11] 4,334,551

[45] Jun. 15, 1982

[54] CONNECTOR

[75] Inventor: Robert D. Pfister, Cary, N.C.

[73] Assignee: Becton Dickinson & Company, Paramus, N.J.

[21] Appl. No.: 34,855

[22] Filed: Apr. 30, 1979

[51] Int. Cl.³ .............................................. A61M 3/00
[52] U.S. Cl. ............................. 137/614.03; 251/149.8; 128/214.2; 128/247
[58] Field of Search ............... 137/614.03, 614, 68 R; 251/149.5, 149.6, 149.8; 128/202.27, 912, 214 B, 214.2, 213 A, 214 R, 247

[56] References Cited

U.S. PATENT DOCUMENTS

| | | | |
|---|---|---|---|
| 2,054,349 | 9/1936 | Wantz | 251/149.5 |
| 2,386,270 | 10/1945 | Samiran | 251/149.6 |
| 2,546,672 | 3/1951 | LeClair | 251/149.7 |
| 2,753,195 | 7/1956 | Palmer | 137/614.03 |
| 3,230,964 | 1/1966 | Debrotnic et al. | 251/149.5 |
| 3,359,015 | 12/1967 | Zahuranec | 251/149.8 |
| 3,538,950 | 11/1970 | Porteners | 251/149.6 |
| 3,853,127 | 12/1974 | Spaderman | 128/214.4 |
| 3,896,853 | 7/1975 | Bernhard | 251/149.5 |
| 3,902,489 | 9/1975 | Carter | 128/214 R |
| 3,977,403 | 8/1976 | Patel | 128/221 |
| 3,986,508 | 10/1976 | Barrington | 128/214.2 |
| 4,019,512 | 4/1977 | Tenczar | 128/214 R |
| 4,022,205 | 5/1977 | Tenczar | 128/214 R |
| 4,080,965 | 3/1978 | Phillips | 128/214 D |
| 4,136,466 | 1/1979 | Wrue | 35/17 |
| 4,143,853 | 3/1979 | Abramson | 251/149.1 |
| 4,195,632 | 4/1980 | Parker et al. | 128/272 |
| 4,256,106 | 3/1981 | Shoor | 128/247 |

OTHER PUBLICATIONS

"A New Sterile Connector for the Chronic Ambulatory Peritoneal Dialysis (CAPD)", Affeld et al., 25th Annual Meeting of ASAIO.

Primary Examiner—A. Michael Chambers
Attorney, Agent, or Firm—Louis E. Marn; Elliot M. Olstein

[57] ABSTRACT

A reusable connector which is provided with a deformable barrier at the open connecting end thereof which maintains the sterile integrity of the interior portions. The deformable barrier includes a preformed opening (or openings) which is normally closed and which can be opened by application of a deformation force, with the opening being reclosed upon release of such force. Connection to a sterile fluid source is made through a mating connector having a similar deformable barrier for maintaining internal sterile integrity. The external surfaces of the barriers are sterilized after connecting the connectors, and after sterilization is complete, a deformation force is applied to the barriers to permit material flow between the interior portions of the connectors.

13 Claims, 11 Drawing Figures

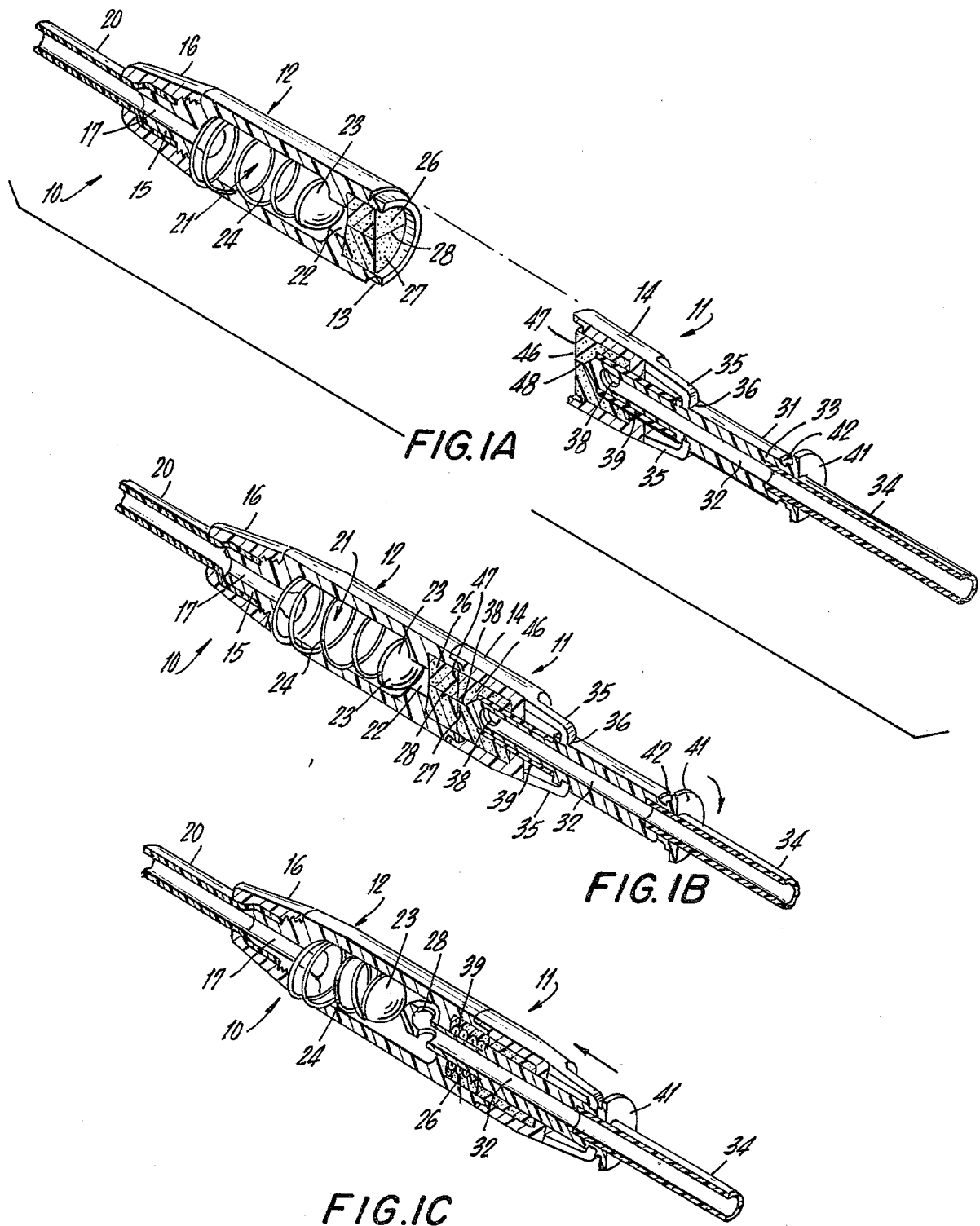

CONNECTOR

This invention relates to connectors, and more particularly to sterile connectors.

Connectors are known in the art for transferring fluid from one location to another. Thus, for example, in peritoneal dialysis, it is necessary to transfer sterile dialysis fluid from a source to the peritoneal cavity. In the case where there is an indwelling catheter in the peritoneal cavity, it is necessary to sterilize the connector attached to the catheter prior to each use. The connectors currently available in the art are difficult to sterilize, and in addition have a high risk of contamination even though sterilized prior to each use.

The present invention is directed to providing new and improved sterile connectors.

In accordance with one aspect of the present invention, there is provided a terminal connector which is capable of being used and reused under sterile conditions. More particularly, the terminal connector is comprised of a housing, the interior of which is adapted to being connected to a device which is to receive sterilized material from the housing interior. The housing interior is under sterile conditions, and such sterilized interior is separated from an open connecting end of the connector by a deformable barrier, which is preferably recessed within the housing, and which maintains the sterile integrity of the housing interior. The deformable barrier includes at least one preformed opening which is normally closed and which can be opened upon application of a deformation force to the barrier, with the opening being reclosed upon release of such deformation force. Although the exterior surface of the barrier is non-sterile, the portions of the connector inward of the exterior barrier surface are under sterile conditions, and the barrier maintains such sterile integrity. The external surface of the barrier is preferably smooth to facilitate subsequent sterilization thereof. In using the connector, only the exterior surface of the barrier need be sterilized, and the barrier subsequently subjected to a deformation force to open the preformed opening (or openings) to establish communication between the interior portions and a mating connector. In accordance with the preferred aspect of the present invention, sterilization of such exterior surface is completed after connection of the connector to a mating connector, and prior to material flow. Upon release of the deformation force, the opening in the barrier is reclosed, whereby upon disconnecting of the connector the sterile integrity of the interior portions of the connector as well as connected lines and/or devices is maintained. In this manner, the terminal connector can be reused, without the necessity of sterilizing the entire interior of the connector.

The terminal connector of the present invention is preferably designed and employed in a manner such that upon opening of the opening in the barrier, communication between the exterior surface of the barrier and presterilized portions of the connector, associated devices and sterile material flow is minimized to thereby minimize the chances of contamination from incomplete sterilization of the exterior barrier surface. More particularly, the terminal connector is preferably designed and employed in a manner such that sterilized material and/or sterilized portions are in communication with the exterior surface of the deformable barrier essentially only at the perimeter of the preformed opening (or openings) therein.

In accordance with another aspect of the present invention, there is provided a pair of mating terminal connectors which are adapted to being connected to each other to establish communication between material flow lines, at least one of the terminal connectors being reusable. Each of the terminal connectors is comprised of a housing, the interior of which is adapted to being connected to a material flow line or device. Each of the housing interiors is under sterile conditions, with each housing including a deformable barrier, preferably recessed in the housing, which separates the housing interior from the open connecting ends thereof to maintain the sterile integrity of such interiors. Each of the deformable barriers includes at least one preformed opening which is normally closed and which can be opened upon application of a deformation force to the barrier, with the opening being reclosed upon release of the deformation force. The barriers are positioned within the connector in a manner such that after connection thereof and/or application of the deformation force the exterior surfaces thereof are in contact with each other, with the respective openings being positioned so that material flow communication can be established between the connectors. The exterior surfaces of the barriers are designed in a manner such as to facilitate such contact; e.g., smooth surfaces.

One of the connectors includes within the sterile housing interior a deforming means, which upon connection of the pair of connectors, can be employed to deform the deformable barriers of both connectors to open the preformed openings thereof and place the interiors of the connectors in material flow communication with each other.

In operation, the connectors are connected to each other and the exterior surfaces of the barriers of the connectors are sterilized, while connected, in order to minimize any chances of contamination from the external environment. The deforming means is then operated to deform both barriers, with the connection between the connectors being such that the barriers in at least the areas around the openings therein, being in exterior surface contact with each other while the openings therein are opened so that communication between the interiors of the connectors is essentially only through the openings in each of the barriers. More particularly, the exterior surfaces of the barriers in at least areas around the openings therein are essentially sealed against each other during material flow communication between the connectors to thereby essentially eliminate any communication between the housing interiors (or component parts thereof) and the exterior surfaces of the barriers, except at the immediate perimeter of the openings therein. In this manner, although the exterior surfaces of the barriers have been sterilized prior to opening of the openings in the barriers, there is essentially no communication between such exterior surfaces and the housing interiors and material flowing therethrough to thereby minimize the possibility of any contamination of the sterilized housing interiors or sterilized material flowing therethrough by contaminants which may be present on the exterior surfaces of the barriers.

In accordance with a preferred embodiment, the deforming means which is normally positioned in the interior of the housing of one of the connectors is in the form of a sterilized plunger. After connection of the connector pair, and subsequent sterilization of the exterior barrier surfaces, the plunger deforms the barriers by being advanced through the preformed openings of both barriers and then enters the interior of the housing of the other connector to establish material flow communication. In accordance with the preferred embodiment, the plunger only contacts the exterior of the barriers at the perimeter of the preformed openings, and as a result of the barriers being in surface contact with each other in at least the area around the openings therein, the exterior surfaces of such barriers are not in communication with the respective housing interiors or the plunger. The plunger is hollow and is connected to a flow line whereby material flows between the interior of the plunger and the interior of the other connector. After flow is complete, the plunger is withdrawn through the opening of the barrier of at least the other connector to thereby release the deformation force on the barrier of the other connector which closes the preformed opening therein to thereby maintain the sterile integrity of the housing interior of the other connector upon disconnection of the connectors.

The invention will be further described with respect to preferred embodiments thereof illustrated in the accompanying drawings, wherein:

FIGS. 1A through 1C illustrate one embodiment of the connectors of the present invention;

Figure 2A:
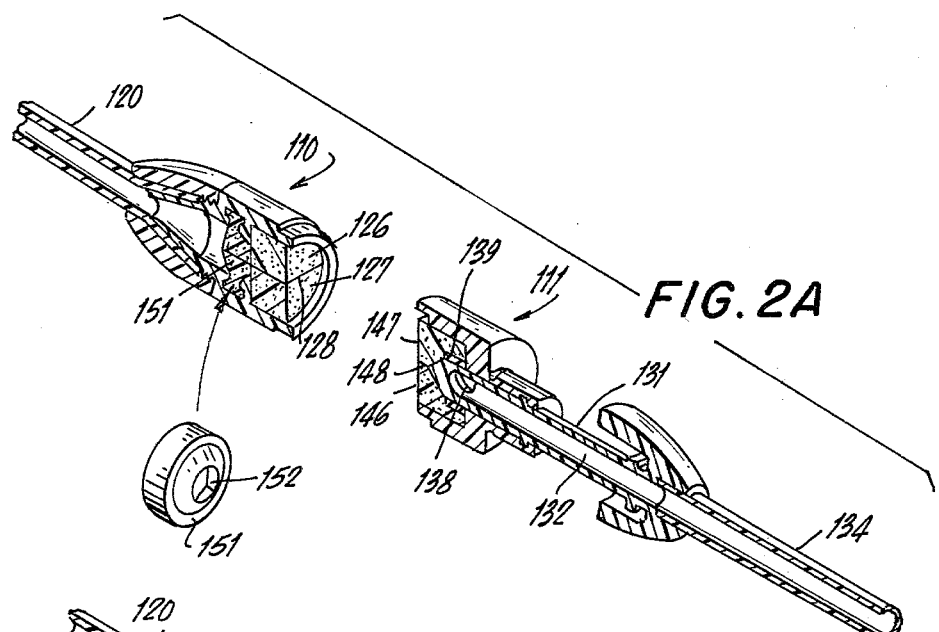
FIGS. 2A through 2C illustrate another embodiment of the connectors of the present invention.

It is to be understood, however, that the scope of the invention is not to be limited by the preferred embodiments.

Referring to FIGS. 1A through 1C of the drawings, there is shown a pair of mating terminal connectors 10 and 11, with at least connector 10 being a reusable connector. The connectors 10 and 11 can be constructed, for example, from a suitable plastic. The terminal connector 10 is comprised of a main tubular body portion 12, which at the open connecting end thereof has a neck portion 13 which is adapted to be telescopically received in the interior of the open connecting end of tubular main body portion 14 of connector 11 to provide a snap-fit connection therebetween. The snap-fit connector is preferably designed to provide a hermetic seal to minimize the possibility of contamination from the surrounding environment after connection.

The main body portion 12 of connector 10, at the end opposite to the connecting end thereof, includes an elongated portion 15, which is inserted, for example, into a catheter 20, which is to receive sterilized fluid. The catheter 20 may be maintained in position by suitable fastening means, such as a threaded connector 16 having interior threads which are received by corresponding threads on the exterior of elongated portion 15.

The elongated portion 15 includes an axial interior channel 17, which is in fluid flow communication with the interior of catheter 20, and the interior chamber 21 within main body portion 12. The chamber 21 is in fluid flow communication with the open connecting end of connector 10 through an axial channel 22, which is normally closed by valve means in the form of a ball valve 23 which is connected to and seated against the passage by a conical spring 24.

The interior of the open connecting end of main body portion 12 is provided with a deformable barrier means in the form of a split deformable resilient foam block 26, which is recessed inwardly from the open end so as to prevent accidental contact therewith when handling the connector. Thus, the main body portion functions as a shield to protect the deformable barrier means 26. The split foam defines a preformed opening 28, which is normally closed, and which can be opened by application of a deformation force to the foam block 26. Thus, for example, by applying a force at the preformed opening, the split sections are outwardly deformed and a member can be inserted through the preformed opening. Upon withdrawal of the member, as a result of the resiliency of the foam, opening 28 is closed. The foam block 26 is seated against passage 22 and the interior wall of the main body portion 12 to effectively close the interior of the connector from the atmosphere and thereby maintain sterile integrity. Thus, all interior portions of the connector and associated tubing inward of the planar exterior surface 27 of foam block 26 are sterile, and the foam block functions to maintain such sterile integrity.

The foam block is preferably impregnated with a sterilizing fluid (a bacterialcidal fluid) which helps prevent entry of contaminants into the sterile interior. A suitable sterilizing liquid is polvinylpyrrolidone iodide (BETADINE). It is to be understood, however, that preimpregnation is not required. For example, the foam can be formed from both open cell and closed cell foam to aid in preventing entry of airborne contaminants. In addition, if sterilization prior to use, as hereinafter described, is effected with a sterilizing liquid, the foam will retain such liquid after disconnection to aid in maintaining sterile integrity.

The connector 10 is generally provided with a suitable cap to close the open end thereof when not being used to further reduce the chances of contamination.

The main body portion 14 of connector 11 is provided with a deforming means in the form of a hollow plunger 31 having an internal passage 32 into which suitable tubing, such as plastic tubing 34 is bonded, with the tubing 34 being in fluid flow connection with a source of sterilized fluid. The forward portion of plunger 31 is within the hollow interior of connector 11, and the remaining portion thereof extends rearwardly therefrom. The plunger 31 is maintained in position by tabs 35 which extend inwardly from the main body portion 14 and are received in corresponding notches 36 on the exterior surface of the plunger. The tabs and notches are constructed in a manner such that by rotation of the plunger 31, the plunger is released from the tabs 31 to permit axial movement thereof.

The forward end of plunger 31 is provided with an outlet in the form of an opening or orifice 38, which is normally closed by a cylindrical sleeve 39, which fits over the forward end of plunger 31. The sleeve 39 is constructed and applied to the plunger in a manner such that upon application of an appropriate force, as hereinafter described, the plunger 31 can be moved relative to sleeve 39 to open orifice 38. Thus, for example, the sleeve 39 can be formed of an elastomeric material, such as rubber. As shown, the sleeve 39 closes orifice 38 and prevents fluid from flowing from the passage 32 into the interior of connector 11.

The rearward end of plunger 31 is provided with an enlarged head 41 for facilitating operation thereof, and a circular groove which is adapted to receive tabs 35 for locking the plunger in position after advancement thereof, as hereinafter described.

The open connecting end of connector 11 is closed by a deformable barrier means in the form of a split deformable resilient foam block 46, which is recessed inwardly from the open end so as to prevent accidental contact therewith when handling the connector. The split foam defines a preformed opening 38 which is normally closed and which can be opened by application of a deformation force to the foam block 36. The foam block 46 is seated against the internal surfaces of the main body portion 14 to effectively close the interior of connector 11 (including the portions of the plunger therein) from the atmosphere and thereby maintain sterile integrity. Thus, all interior portions of the connector and associated tubing inward of the planar exterior surface 47 are sterile, and the foam block 46 functions to maintain such sterile integrity.

The foam blocks 26 and 46 are positioned in the connectors 10 and 11, respectively, in a manner such that when the connectors 10 and 11 are connected to each other the exterior surfaces 27 and 47 thereof in at least the area of the openings therein are in contact with each other; note FIG. 1B.

In operation, for example, the terminal connector 10 is connected to catheter 20 for introducing suitable dialysis fluid into the peritoneal cavity. The portions of the connector 10 inward of the exterior surface 27 of the foam block 26, as well as the associated catheter are sterile.

The connector 11 and associated tubing 34 are connected to a suitable source of dialysis fluid (not shown). The portions of connector 11 inward of the exterior surface 47 of foam block 46, including the portions of a plunger 31 therein as well as the interior portions of the plunger and tubing are sterilized.

If the foam block 26 has not been previously impregnated with a sterilizing fluid, a sterilizing fluid is applied thereto and connectors 10 and 11 are connected to each other thereby placing the foam blocks 26 and 46 in contact with each other (note FIG. 1B). If the foam block 26 has been preimpregnated and block 46 is dry, foam block 46 receives sterilizing fluid from block 26 by a "wicking" action. Such contact is maintained for a period of time sufficient to insure that the exterior surfaces 27 and 47 of such foam blocks are sterilized by the sterilizing fluid. As should be apparent, sterilization of such exterior surfaces is effected after connection of the connectors, thereby minimizing the risk of any contamination of such surfaces subsequent to sterilization.

After sterilization of such surfaces is completed, the plunger 31 is rotated to release the plunger 31 from tabs 35, and the plunger is advanced to deform sequentially foam blocks 46 and 26, with the plunger advancing sequentially through the preformed openings 48 and 28. The advancement of plunger 31 through channel 22 of connector 10 unseats ball valve 23 by compressing spring 24. The plunger 31 is constructed with a diameter such that the exterior surface of plunger 31 moves in sliding contact with the interior of channel 22, whereby the sleeve 39 is prevented from entering channel 22, and the plunger is moved relative thereto. The plunger 31 has a slight outward taper whereby the plunger is seated in passage 22 to prevent fluid flow therethrough. In this manner, sterilizing fluid on the foam blocks cannot flow into interior 21 and dialysis fluid is prevented from flowing outwardly from interior 21. The plunger 31 is maintained in the advanced position by the locking action of tabs 35 in groove 42. FIG. 1C illustrates the connector with the plunger in the advanced position.

The orifice 38 of plunger 31 is now open, whereby the sterilized fluid can flow from a sterilized fluid source through tubing 34, passage 32, opening 38, chamber 21 and passage 17 to the indwelling catheter 20, all of which have been previously maintained under sterilized conditions.

As hereinabove described, after connecting of connectors 10 and 11, the only interior portions which were not maintained in a presterilized state are the exterior surfaces of foam blocks 26 and 46, and such blocks are sterilized after connection and immediately prior to fluid flow. In addition, and most important, during use of the connectors, such exterior portions of the foam blocks are essentially isolated from the presterilized interior portions in that the surfaces are maintained in contact with each other, and the plunger, when advanced, contacts such exterior surface portions only at the immediate external perimeter of the preformed openings to thereby minimize the possibility of contamination. Thus, there is essentially no communication between the portion of the connector sterilized by a user and the internal flow portions which have been presterilized, and which must be maintained under sterile conditions to prevent infection.

After fluid flow is completed, the connector 11 may be disconnected from connector 10 and the plunger withdrawn therefrom, which releases the compressive force on spring 24 and seats ball valve 23 to close passage 22 to prevent any fluid flow from chamber 21 therethrough. In addition, the deformation force is released from foam block 26 to close opening 28 and maintain the sterile integrity of the connector inwardly thereof. Alternatively, the plunger 31 may be withdrawn to the position of FIG. 1B to close the openings, followed by disconnection of the connectors. In this manner, the connector 10, which is connected to an indwelling catheter, can be reused in the manner hereinabove described in that sterile integrity is maintained upon disconnection.

Figure 2B:
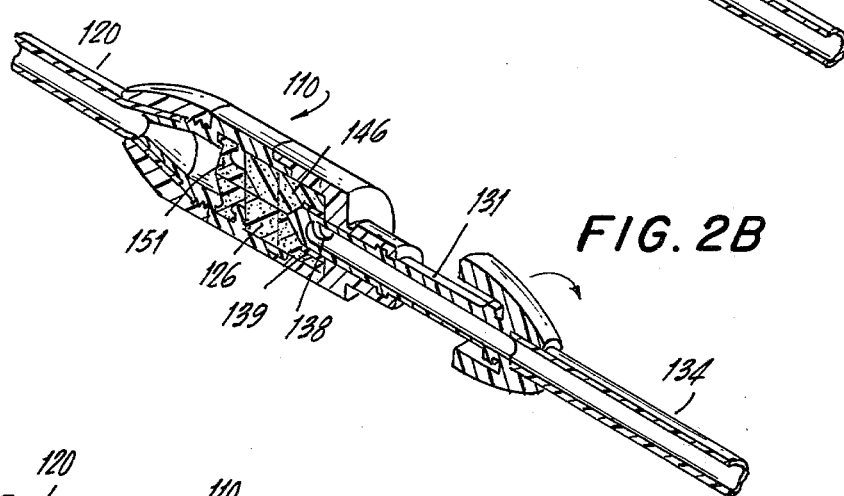
Figure 2C:
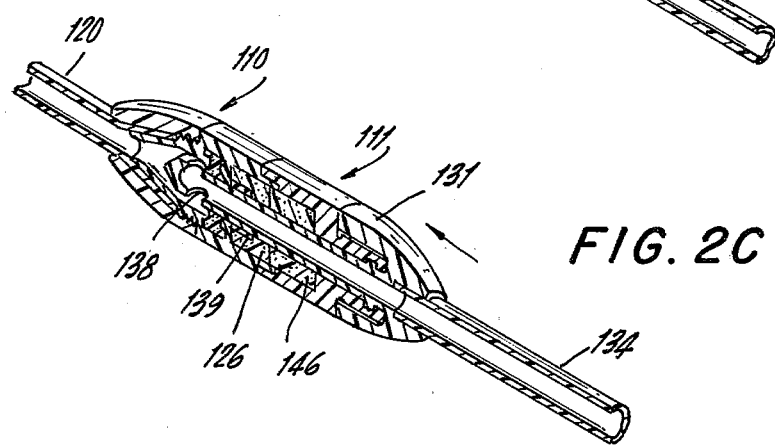

Another embodiment of the connector of the present invention is shown in FIGS. 2A through 2C, and such connector is constructed and is employed in a manner similar to the connector described with reference to FIGS. 1A through 1C. As a result, a detailed description of such connector is not required for a complete understanding of such embodiment.

Referring to FIGS. 2A through 2C, there is shown a reusable connector 110 and a connector 111, with the connector 111 being constructed in a manner essentially identical to the connector 11 of the embodiment of FIGS. 1A through 1C. Thus, as shown, the connector 111 includes a plunger 131 having an internal passage 132 connected to suitable tubing 134 and having an orifice or opening 138 which is normally covered by a rubber sleeve 139. The sterile integrity of the interior of the connector, and associated equipment, is maintained by a deformable barrier means in the form of a split foam block 146 having a flat exterior surface 147, with the split block defining a preformed opening 148, which is normally closed, and which is opened upon application of a deformation force.

Similarly, the reusable connector 110 has the open connecting end thereof closed by a deformable barrier means in the form of a split foam block 126 having a flat exterior surface 127 with the split foam block defining a preformed opening 128, which is normally closed, and which is opened upon application of a deformation force. The foam block 126 maintains the sterile integrity of the interior portions of the connector and associated tubing.

The embodiment of FIGS. 2A through 2C differs from the embodiment of FIGS. 1A through 1C basically with respect to the use of a sphincter diaphragm, instead of a spring loaded ball valve, for preventing fluid from flowing outwardly from or inwardly to the internal chamber 121. As shown, the sphincter diaphragm 151 includes a preformed opening or slit 152 which can be opened upon application of a deformation force. The sphincter diaphragm 151 is in sealing contact with appropriate internal surfaces of the connector 110 to provide a fluid tight seal which prevents fluid flow between chamber 121 and the exterior of the connector.

The connector of FIGS. 2A through 2C is employed in a manner similar to the connector of FIGS. 1A through 1C. Thus, if foam block 126 has not been previously impregnated with a sterilizing fluid, a sterilizing fluid is added to the external surface thereof, and connectors 110 and 111 are connected to each other; note FIG. 2B. The external surfaces of the foam block are in contact with each other, and such external contact is maintained for a time sufficient to sterilize such external surfaces. After sterilization is completed, plunger 131 is advanced through the preformed openings in foam blocks 146 and 126, and through the preformed opening in diaphragm 151 whereby the plunger enters chamber 121 of connector 110. The exterior diameter of plunger 131 is such that it fits through the narrow opening 122 in connector 110 in sliding contact therewith, whereby at such point the plunger 131 moves relative to the sleeve 139 to thereby open orifice 138; note FIG. 2C. As should be apparent, sterilized fluid can now flow through the internal passage 132 of plunger 131, and orifice 138 therein, into chamber 121 of connector 110 and into the associated catheter 120. Sterile integrity during such fluid flow is maintained, as hereinabove described with reference to FIG. 1A through 1C. In addition, upon disconnecting of connector 111 or prior withdrawal of plunger 131, the opening 152 in diaphragm 151 is reclosed, and the opening 128 in block 126 is also reclosed to thereby respectively prevent fluid flow into or out of chamber 121 and to maintain the sterile integrity of the interior portions of connector 110, thereby permitting reuse thereof.

Figure 3A:
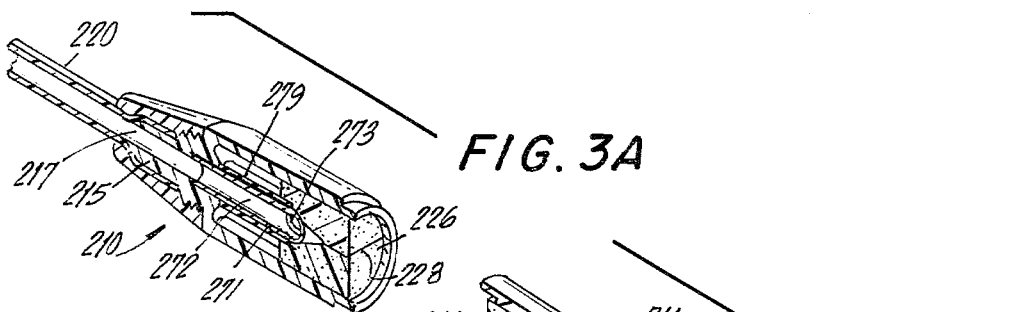
FIGS. 3A through 3C illustrate yet another embodiment of the connector of the present invention.
Figure 3B:
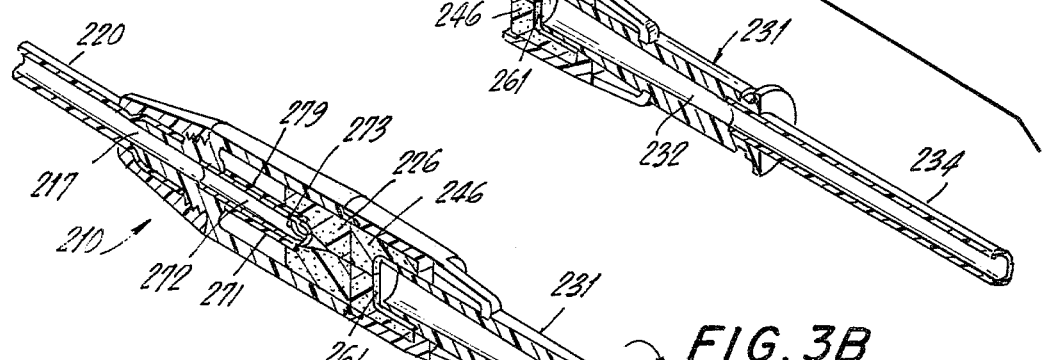
Figure 3C:
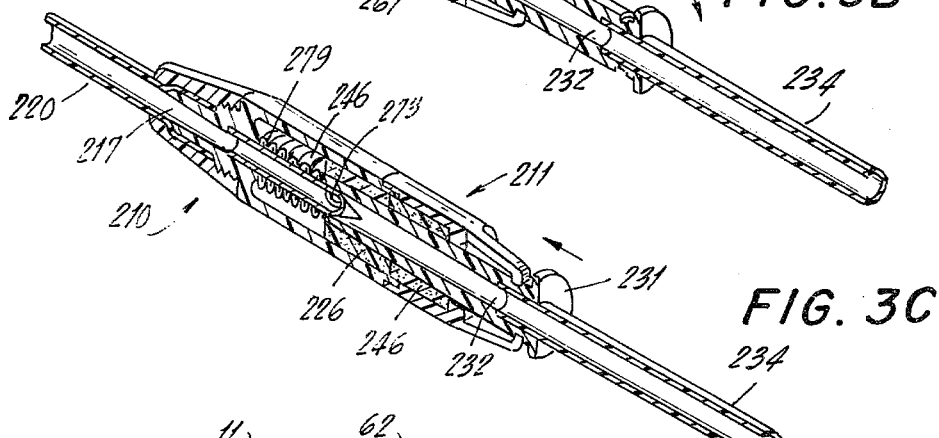

Still another embodiment of the present invention is illustrated in FIGS. 3A through 3C, and in the essential aspects, such embodiment is similar to the previously described embodiments.

Referring to FIGS. 3A through 3C, there is shown a reusable connector 210 and a mating connector 211. The connector 211 includes at the open connecting end thereof a deformable barrier, in the form of a split foam block 246, with the split foam block defining a preformed opening 248. The split foam block 246 functions to maintain sterile integrity within the interior of terminal 211, as hereinabove described.

The terminal connector 211 is further provided with a deforming means in the form of a plunger 231 having an internal passage 232 which is connected to associated tubing 234. In the embodiment of FIGS. 3A through 3C, the internal passage 232 has an open axial end, which is closed by a pierceable closure means in the form of a rubber septum 261.

The reusable connector 210 has the open connecting end thereof closed by a deformable barrier means in the form of a split foam block 226 which defines a preformed opening 228, which is normally closed, with the foam block 226 maintaining the sterile integrity of the interior of the connector as hereinabove described.

The elongated portion 215 of connector 210 is connected to an appropriate catheter 220 which communicates with the internal passage 217 in elongated portion 215. In the embodiment of FIGS. 3A through 3C, the internal passage 215 is provided with a hollowlance element 271 which extends outwardly therefrom into the interior of the connector, with the interior of the lance element 271 defining a flow passage 272 in fluid flow communication with the interior passage 217 and the interior of catheter 220. The forward end of lance 271 is provided with an oulet in the form of an opening or orifice 273, which is normally covered by a cylindrical sleeve 279 which fits over the forward end of lance 271. The sleeve 279 is formed of a resilient material which can be compressed rearwardly on the lance element to thereby open the orifice 273. In addition, upon release of the compressing force, such sleeve resumes its normal position so as to close orifice 273.

The connector of FIGS. 3A through 3C is employed in a manner as hereinabove described. Thus, sterilizing fluid, if not present in the foam block, is applied to the external surface, and the connectors connected to each other with the foam blocks 226 and 246 being in surface contact with each other, as shown in FIG 3B. After sterilization of the external surfaces of the foam blocks is completed, plunger 231 is advanced through the preformed openings in the foam blocks and upon entry into the terminal connector 210, the septum 261 is pierced by lance 271. Further advancement of the plunger compresses sleeve 279 to thereby open orifice 273 in the lance element 271. As shown in FIG. 3C, sterilized fluid can now flow from tubing 234 through internal passage 232 in plunger 231, through orifice 273 in lance element 271 and then through the internal passages 272 and 217 into catheter 220. As hereinabove described, such connection is made while maintaining sterile conditions.

After fluid transfer is completed, the connectors 211 and 210 may be disconnected (plunger 231 can be withdrawn prior to disconnection), with such disconnection (or withdrawal) releasing the compressive force on sleeve 279 to thereby cause the sleeve to resume its normal position of closing opening 273 in lance element 271 and also releasing the deforming force on the foam 226 to thereby close preformed opening 228 and thereby maintain sterile integrity.

The mating connectors including the plunger element (connectors 11, 111 and 211 of the drawings) are preferably single use connectors, with such connector and associated equipment (for example, tubing and bag for dialysis fluid) being included in a presterilized package. Such mating connector and associated equipment can be removed from the sterilized package and connected to the reusable mating connector for use as hereinabove described.

Figure 4B:
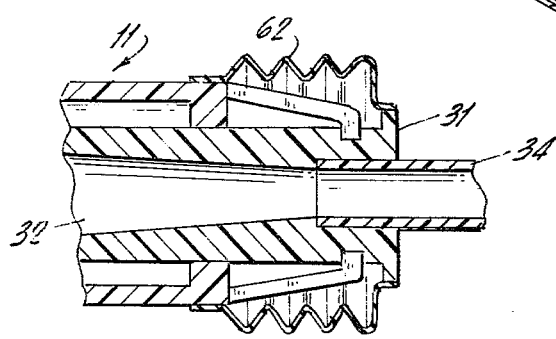
FIGS. 4A and 4B are a partial view of another modification.
Figure 4A:
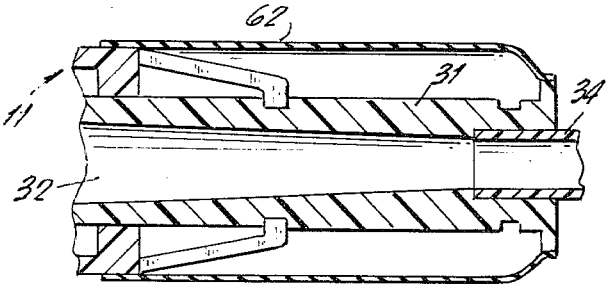

It is also possible to employ such mating connector for more than a single use; i.e., as a reusable connector. In such use, the plunger would be withdrawn prior to disconnection, with such plunger withdrawal reclosing the openings in the deformable barriers in both mating connectors, whereby sterile integrity is maintained after disconnection. In employing the connector including the plunger element as a reusable connector, means should be provided for insuring the sterility of the portions of the plunger which are normally external of the connector interior; i.e., exposed to ambient environment, and which enter the sterile interior upon advancement of the plunger. Such sterility can be maintained, for example, by providing a protective cover for the portions of the plunger which are exterior of the connector in the withdrawn position. Thus, for example, as shown in FIGS. 4A and 4B, which illustrate only a portion of the connector including the plunger element, the plunger 31 is provided with a cover 62 which is sealed at one end to plunger head 41 and at the other end to the connector 11. The cover 62 is formed of a suitable deformable resilient material, such as an elastomeric material, and such cover effectively seals the plunger from the atmosphere. Upon advancement of the plunger (FIG. 4B), the cover 62 is deformed into a bellowslike shape and upon retraction of the plunger, the cover resumes the shape shown in FIG. 4A. In this manner, the sterile integrity of the plunger which enters and is withdrawn from the sterile interior of the connector is maintained. It is to be understood that the cover could take a form other than that particularly shown. It may also be possible, in some cases, to reuse the connector including the plunger element without providing a cover. Thus, for example, in some cases it may be possible to provide an appropriate wiping action to the plunger exterior (by an o-ring) to prevent contaminants from entering the connector interior when advancing the plunger.

The exterior surfaces of the deformable barriers are sterilized subsequent to connection of the mating connectors. Although such sterilization has been particularly described with reference to the use of a sterilizing liquid, it is to be understood that such sterilization could be accomplished in other ways, for example, by heat.

Although the connectors have been described with particular reference to peritoneal dialysis with the reusable connector being attached to an indwelling catheter, it is to be understood that the connectors are also suitable for other uses where sterile connection and disconnection is desired; for example, for transfer of intravenous fluid, extracorporeal blood lines, plasma fractionation, etc. The above uses and others should be apparent to those skilled in the art.

Similarly, the connectors hereinabove described can be modified within the spirit and scope of the invention. Thus, for example, the deformable barrier having a preformed opening or openings may be constructed from other than foam blocks, provided the material is deformable and sufficiently resilient to reclose the preformed opening(s). For example, the deformable barrier need not be formed entirely of foam. Thus, the deformable barrier can be a composite comprised of foam with a suitable backing to provide structural strength. Similarly, preformed openings can be provided by other than the use of split sections.

As also should be apparent the mechanics for mating the connectors and/or deforming the barriers can be modified within the spirit and scope of the invention.

It is also to be understood that although the connector has been particularly described with reference to a sterile connector, the connector could be employed where sterile integrity is not required.

It is also to be understood that the connector including the deformation means (plunger in the drawings) could be employed as a reusable connector; e.g., connected to the catheter.

As a further modification, if one of the connectors is to be employed as a single use connector, the connecting end could be closed by other than a barrier with a preformed opening. For example, the end could be closed by a rupturable or pierceable closure, which is ruptured or pierced by the movable deformation means (after connection of the pair). The mating reusable connector would include the deformable barrier, which would be reclosed as hereinabove described.

The connectors can be employed for establishing material flow as a solid, liquid or gas, preferably a liquid or gas.

The present invention is particularly advantageous in that fluid connection is effected, while minimizing chances of contamination both before, during and subsequent to connection. In addition, there is provided a reusable connector which requires only minimal sterilization prior to each use thereof. Furthermore, such sterilization is effected subsequent to connection thereby minimizing the risk of contamination. As a further advantage, the connection is made in a manner such that contact between portions of the connector which are sterilized by the user and presterilized portions are minimized or in effect essentially eliminated. In addition, here is provided automatic closing of the flow path into the interior of the reusable connector in the event of an accidental disconnection. These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

I claim:

1. A sterile connection assembly, comprising:
a pair of terminal connectors for connection to each other, each of said connectors including a housing having a sterile interior and an open connecting end; each of said connectors including an openable closure means for closing the housing interior from the open connecting end and maintaining sterile integrity, each of said closure means comprising a deformable resilient barrier means including at least one preformed opening which is normally closed and which is opened upon deforming the barrier means and which is closed upon release of deformation by the resiliency of the barrier means, and one of said housings including an integral movable deforming means in the interior thereof, said deforming means after connection of the connectors being movable relative to said one of said housings to apply a releasable deformation force to the barrier means in each of said connectors which deformation force opens the at least one preformed openings in the barrier means of each of said connectors.

2. The assembly of claim 1 wherein the movable deforming means is comprised of a plunger which deforms said barrier means by advancement through the preformed openings and into the interior of the other of the pair of connectors.

3. The assembly of claim 2 wherein upon connection of the connectors the deformable barrier means are in contact with each other in at least the areas thereof having the openings therein.

4. The assembly of claim 3 wherein each of said deformable barrier means is recessed within the respective housing interiors.

5. The assembly of claim 4 wherein the plunger includes an internal flow passage adapted to being connected to a flow line, said plunger including an opening which is in communication with the internal passage upon advancement of the plunger into the interior of the other of the pair of connectors to permit material flow therethrough.

6. The assembly of claim 5 wherein at least a portion of the deformable barriers of each of the pair of connectors which includes the at least one opening is comprised of foam.

7. The assembly of claim 6 wherein at least the deformable barrier of the other of the pair of connectors is impregnated with a sterilizing liquid.

8. The assembly of claim 4 wherein the pair of connectors include means for hermetically connecting the connectors to each other.

9. The assembly of claim 8 wherein each of the deformable barrier means is comprised of a split foam block.

10. The assembly of claim 9 wherein the interior of the other of the pair of connectors includes a valve means between the deformable barrier means and the housing interior, said valve means closing fluid flow communication between the housing interior and the open connecting ends and said valve means being opened by advancement of said plunger.

11. The assembly of claim 10 wherein the valve means is comprised of a ball and spring.

12. The assembly of claim 10 wherein the valve means is comprised of a sphincter diaphragm.

13. The assembly of claim 9 wherein the interior of the housing of the other of the pair of connectors includes a lance element, said lance element including an internal passage adapted to being connected to a flow line and an opening for communication between the internal flow passage and exterior of the lance element; a movable cover closing said opening, said plunger including an internal flow passage adapted to being connected to a flow line, said plunger internal passage having an open end; a pierceable cover being pierced by the lance element when the plunger is advanced into the interior of the other of the pair of connectors and said pierceable cover moving said movable cover to open the opening in the lance element, said lance element being telescopically received in the internal passage of the plunger to establish fluid flow communication between the connectors through the internal flow passages in the lance element and plunger.

* * * * *